(12) United States Patent
Vickery (10) Patent No.: US 10,512,473 B2
(45) Date of Patent: Dec. 24, 2019

(54) SURGICAL TOOL (71) Applicant: DENTMED LIMITED, Bristol (GB)

(72) Inventor: Ian Malcolm Vickery, Bristol (GB)

(73) Assignee: DENTMED LIMITED, Bristol (GB)

( * ) Notice: Subject to any disclaimer, the term of this patent is extended or adjusted under 35 U.S.C. 154(b) by 101 days.

(21) Appl. No.: 15/799,311

(22) Filed: Oct. 31, 2017

(65) Prior Publication Data

US 2019/0125364 A1 May 2, 2019

(51) Int. Cl.
*A61B 17/16* (2006.01)
*A61B 17/14* (2006.01)
*A61L 31/04* (2006.01)
*A61L 31/14* (2006.01)
*A61B 17/00* (2006.01)

(52) U.S. Cl.
CPC .......... *A61B 17/1622* (2013.01); *A61B 17/14* (2013.01); *A61L 31/048* (2013.01); *A61L 31/14* (2013.01); *A61B 2017/00424* (2013.01); *A61B 2217/007* (2013.01)

(58) Field of Classification Search
CPC ........................... A61B 17/1622; A61B 17/14
See application file for complete search history.

(56) References Cited

U.S. PATENT DOCUMENTS

| | | | |
|---|---|---|---|
| 5,240,339 | A | 8/1993 | DeForest et al. |
| 6,689,146 | B1 | 2/2004 | Himes |
| 7,037,110 | B1 | 5/2006 | Van Hale |
| 2004/0092895 | A1 | 5/2004 | Harmon |
| 2005/0171467 | A1 | 8/2005 | Landman |

FOREIGN PATENT DOCUMENTS

| | | | |
|---|---|---|---|
| GB | 1517286 | | 7/1978 |
| GB | 2367751 | A | 4/2002 |
| GB | 2513427 | * | 10/2014 |
| GB | 2513427 | A | 10/2014 |
| GB | 2517092 | A | 2/2015 |
| JP | 2016098327 | A | 5/2016 |
| RU | 2275293 | C1 | 4/2006 |
| WO | WO 2011/085392 | A1 | 7/2011 |

* cited by examiner

*Primary Examiner* — Olivia C Chang
(74) *Attorney, Agent, or Firm* — Leason Ellis LLP (57) ABSTRACT

A hand-held surgical tool having at least one pad of vibration-absorbent material thereon, the pad being of hydrophobic polyurethane foam made from a polyol and isocyanate composition in which the weight ratio of polyol to isocyanate is from 2.5:1 to 1.5:1. Also a hand-held surgical tool having at least one pad of vibration-absorbent material thereon, the pad having an irrigation duct therethrough connected to means for supplying irrigation fluid to the duct. Also a pad for a hand-held surgical tool, wherein the pad has an irrigation duct therethrough connected to means for supplying irrigation fluid to the duct.

10 Claims, 8 Drawing Sheets

SURGICAL TOOL

FIELD OF THE INVENTION

The present invention relates to a surgical tool which will be hand held.

BACKGROUND OF THE INVENTION

Surgical procedures involving bone regularly require drilling, reaming, or sectioning of bones such as the femur, tibia, radius, ulna, mandible and others.

The techniques involved often require the surgeon to place one or both arms/hands in unusual and awkward positions for lengthy periods of time. When these unusual positions involve the, sometimes lengthy, use of hand held cutting equipment there can be a neurological effect on the palms and fingers of both hands and on the arms.

These peripheral neurological effects can take the form of paraesthesia or anaesthesia which can be intermittent, short term, or more prolonged, they may also become worse during or following multiple operation lists.

Should these symptoms be ignored there can a more generalized hand/wrist muscle weakness which can become progressive.

SUMMARY OF THE INVENTION

The present invention results from the measurement of vibrations from hand held cutting equipment and decade's long clinical use of a closed cell hydrophobic polyurethane foam.

Although this problem has been appreciated for some time there has been little clinical trial to try and prevent these developments until the arrival of medico-legal implications.

At its most general, a first aspect of the present invention provides one or more pads of hydrophobic polyurethane foam, which are mounted on the tool for vibration absorption.

Thus, this aspect of the present invention may provide a hand-held surgical tool having a pad of vibration-absorbent material, the pad being of hydrophobic polyurethane foam made from a polyol and isocyanate composition in which the weight ratio of polyol to isocyanate is from 2.5:1 to 1.5:1.

An irrigation duct may extend through the pad. The duct may terminate at an external surface of the pad, so that the movement of the tool accurately controls the movement of the termination of the irrigation duct, to allow irrigation to be directed to the region desired.

Indeed, the use of such an irrigation duct in a vibration-absorb pad represents a second independent aspect of the invention. This aspect may provide a hand-held surgical tool having at least one pad of vibration-absorbent material thereon, the pad having an irrigation duct therethrough connected to means for supplying irrigation fluid to the duct.

The tool may be a saw having a handle being a first-hand grip and an elongated surface being a second-hand grip. The surgeon will normally use his right hand to hold the handle, and place his left hand on the elongated surface, which is normally an upper surface of the tool, to steady the tool. With the present invention, either or both of the handle and the elongated surface may have a pad mounted thereon.
In the subsequent discussion, the pads will be referred to as VM-A and VM-G and may also be referred to as guards.
The polyurethane foam used in the production of units VM-A and VM-G has been approved for intra cavity use since the 1970's and there was, or has been, no prior art demonstrated.

The polyol composition is as listed below—
Polyoxyalkene
Triethanolamine
Dipropylene glycol
Triethyldiamine
Organo-modified polysiloxanes
C9-11 alcohol ethoxylate
2-{[2-dimethylamino] methylamino} ethanol
The isocyanate composition is—
Methylenediphenyl diisocyanate—MDI The chemical formulations for each of the three samples of the VM-A and VM-G units tested were adjusted in order to confirm the best protection of the palms and fingers and arms from any vibration.

In the polyol and isocyanate composition that forms the, or each, pad;

(i) the polyol may comprise 94.8% by weight polyoxyalkylene triols, 1.8% by weight triethanolamine, 0.2% by weight dipropylene glycol, 0.1% by weight triethyldiamine, 0.4% by weight organo-modified polysiloxanes, 2.1% by weight C9-11 alcohol ethoxylate and 0.6% by weight 2-[[2-dimethylamino)ethyl]methylamino] ethanol, and/or (ii) the isocyanate may (comprise) 50% to 77% by weight diphenylmethanediisocyanate, isomers and homologues thereof, and 23% to 50% by weight isocyanates that are the reaction product of the polyol with methylenediphenyldiisocyanate.

Initial testing VM-A [top guard], and VM-G [bottom guard], using an unspecified chemical formulation resulted in a reduction from 0.73 g to 0.37 g when the top guard was in position and 0.44 g to 0.13 g when bottom guard was in position.

Chemical formulations for three samples of hydrophobic polyurethane for testing against vibrations induced by a hand held battery powered saw with blade attached but with bone cutting/drilling in action.
Top guard—VM-A—aligner.
1.8.5 polyol 3.9 iso.
2.9 polyol 4.5 iso.
3.9 polyol 5 iso.
Bottom guard—VM-G—grip.
1.15 polyol 6.8 iso.
2.12.5 polyol 6.25 iso.
3.12 polyol 6.7 iso.

The three formulations listed above are calculated to increase the "Shore index" for top and bottom guards in the order 1-3—in essence increasing the density of each unit and therefore the absorption of the vibrations induced by the saw.

The top guard has an acrylonitrile butadiene styrene [ABS] onlay positioned directly against the barrel of the saw/drill preventing any vibration reaching the hand and fingers of the operator. The bottom guard also has an acrylonitrile butadiene styrene [ABS] onlay that is spaced from the grip section of the saw/drill. In particular, where the bottom guard covers a trigger of the saw/drill, the onlay is spaced from the trigger of the saw/drill. This means that the operator's fingers are protected from vibration when the operator squeezes the trigger, so that the onlay contacts and depresses the trigger, but that the trigger is able to return to its original position when the operator releases the trigger without significant resistance.

Advantageously, the lower end of the onlay of the bottom guard contacts the lower end of the grip section, so as to provide a pivot point about which the onlay of the bottom guard can pivot when the operator squeezes the trigger.

With this aspect to the overall polyurethane cushion it becomes possible to retain manual dexterity—"feel"—whilst protecting the surgeon's hands.

Measurements have been carried out of the magnitude and frequency of significant vibrations imposed on the hands holding bone cutting and drilling equipment during orthopaedic surgery.

Peak measurements recorded simultaneously from the outer aspects of the distal phalange, the distal metacarpal and the medial metacarpal of the finger of both right and left hands.

When the VM-A and VM-G units are held, a measurement is taken from the outer aspect of the distal phalange of the index finger when this finger is applied to the on/off trigger—this allows seven simultaneous recordings to be taken. Repeated tests during bone cutting may demonstrate total or near total protection from vibrations measured between 5-2000 Hz.

Specialised polyurethane foam with CE & FDS accreditation is used to form two designs of guard—the VM-A & VM-G which are placed between the cutting/drilling instrument and the surfaces of the hands and fingers.

Thus, specific shaped abs onlays are positioned on the external surfaces of the drive shaft of the drill and the grip section each then held in position by polyurethane foam of known chemical specifications.

Both VM-A & VM-G units withstand porous load autoclaving 134 degrees c. 32 psi with a 5 cycle pulsation followed by 50 mb drying cycle without unit distortion.

DETAILED DESCRIPTION OF CERTAIN EMBODIMENTS OF THE INVENTION

Embodiments of the present invention will now be described in detail by way of example, with reference to the accompanying drawings.

Figure 1:
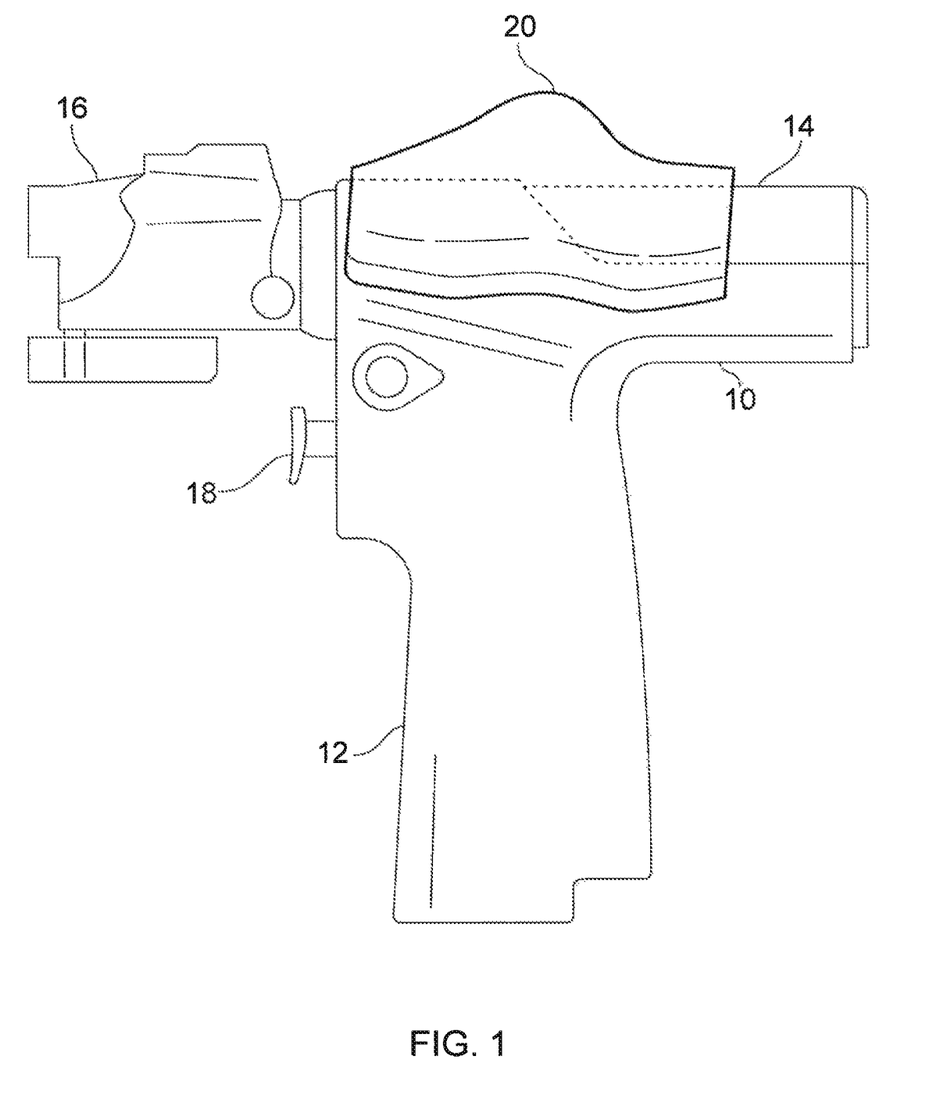
FIG. 1 shows a surgical tool in accordance with one embodiment of present invention.

FIG. 1 shows a surgical tool to which the present invention is applied. The tool has a body 10 with a handle 12 and an elongated upper surface 14. The body 10 is connected to a power head 16. A trigger 18 operated by the surgeon drives the power head 16. Normally, with the saw being driven by the power head 16, to enable cutting, as previously described, but the saw may be replaced by a drill when needed.

In normal use, the surgeon holds the handle 12 in the right hand, to enable to trigger 18 to be operated, and places the left hand on the elongated upper surface 14 to steady the tool. However, the surgeon's hands, particularly the hand on the elongated upper surface 14, are subject to much vibration as previously discussed. Therefore, according to the present invention, at least one vibration absorbing pad is fitted to the tool. In FIG. 1, that pad is pad 20 (VM-A pad) fitted to the elongated upper surface 14 of the tool. Advantageously, vibration absorbing pads are fitted to both the handle 12 and the elongated upper surface 14 of the tool.

Figure 2A:
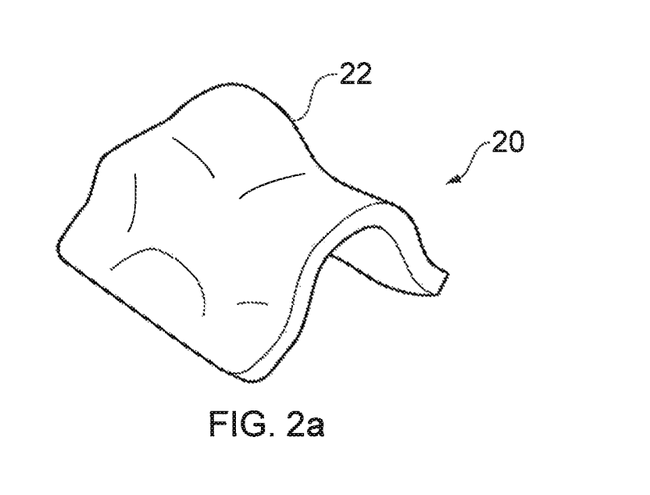
FIGS. 2a to 2f show details of a pad which is part of the surgical tool in accordance with certain embodiments of the invention.
Figure 2B:
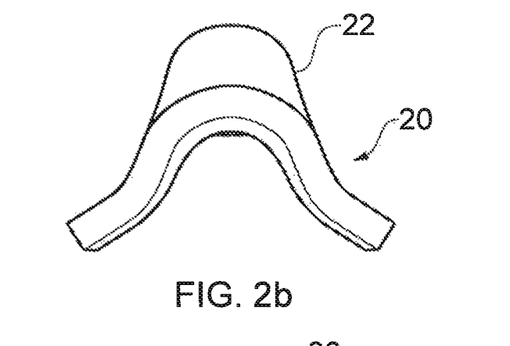
Figure 2C:
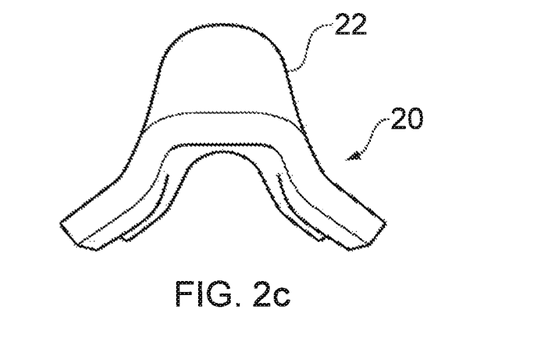
Figure 2D:
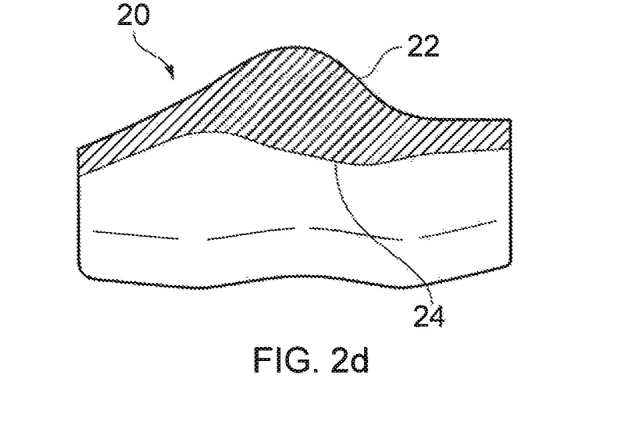
Figure 2E:
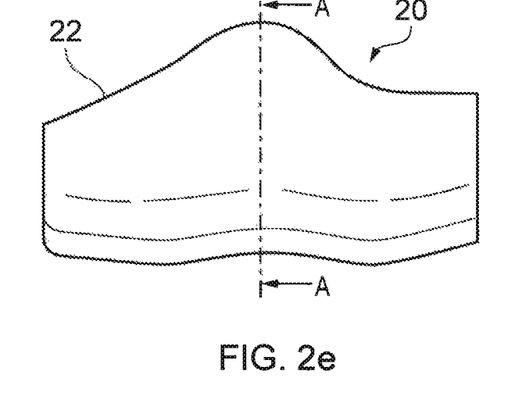
Figure 2F:
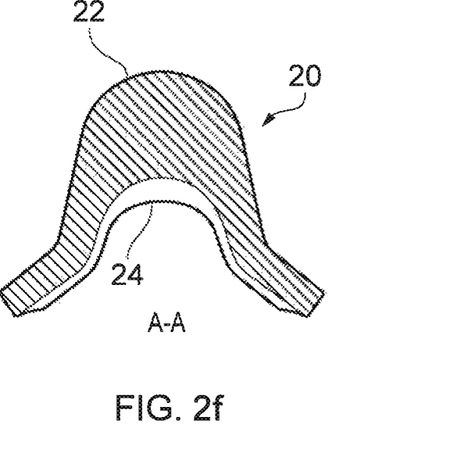

FIGS. 2a to 2f show the pad in more detail. FIG. 2a is a perspective view, FIGS. 2b and 2c are end views, FIG. 2b is a longitudinal sectional view through the pad, FIG. 2e is a side view, and FIG. 2f is a sectional view along the line A to A in FIG. 2e. These views show the general shape of the pad 20, which partially covers the upper surface 14, and lying on the upper surface 14.

The outer surface 22 of the pad 20 is shaped to conform to the surgeon's hand, when that hand is positioned on top of the tool, covering the pad 20, whilst the inner surface 24 conforms to the shape of the elongated upper surface 14 on which the pad 20 is mounted.

Figure 3A:
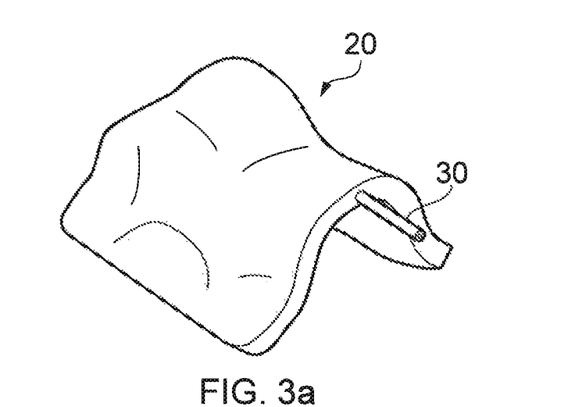
FIGS. 3a and 3b show a modification of the embodiment of FIGS. 2a to 2f to include an optional irrigation duct.
Figure 3B:
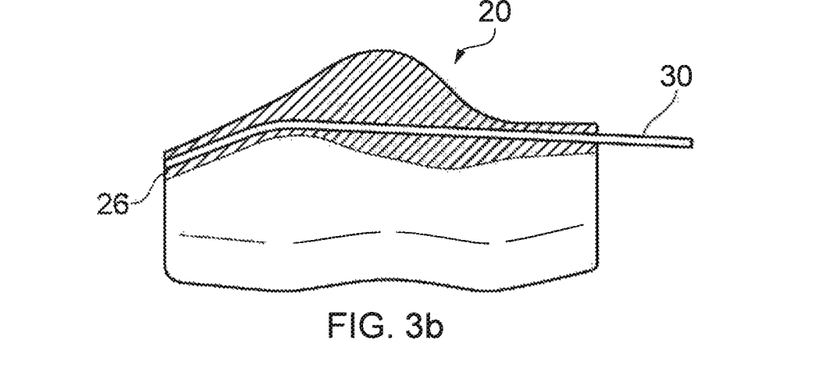
Figure 4A:
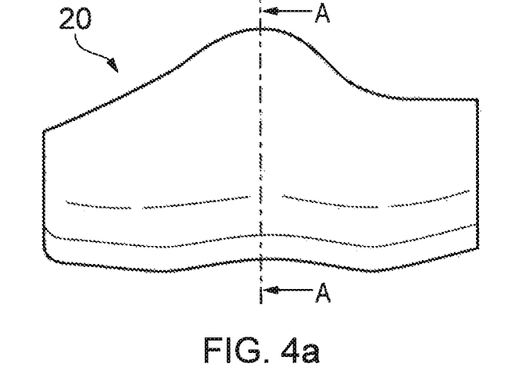
FIGS. 4a to 4d show another modification in which an onlay is included.
Figure 4B:
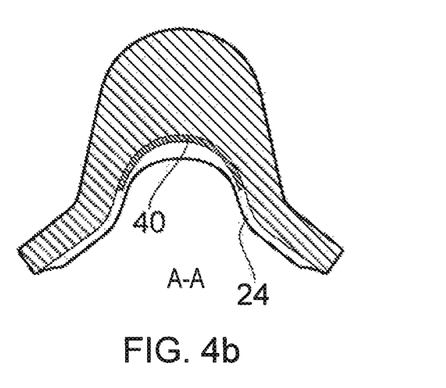
Figure 4C:
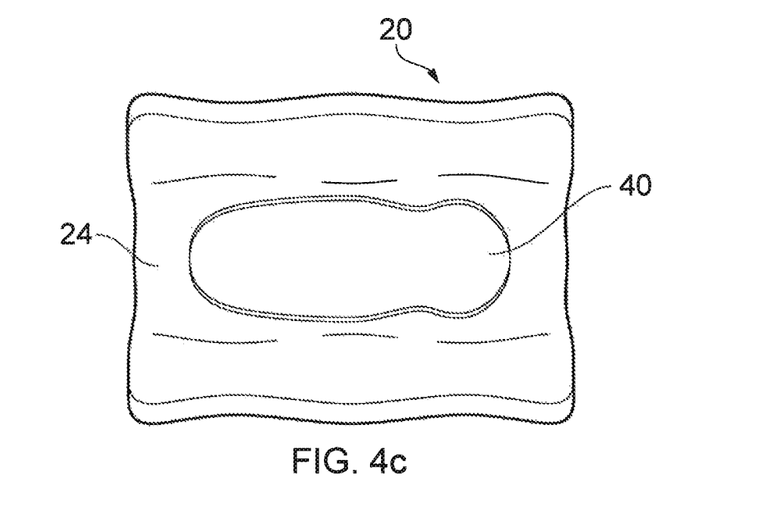
Figure 4D:
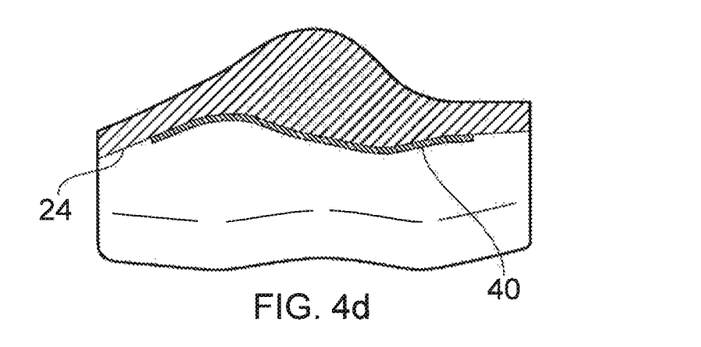

FIGS. 3a and 3b show a modification of the embodiment of FIGS. 2a to 2f, in which there is an irrigation duct formed by a tube 30 which extends through the pad, to terminate at the leading surface 26 of the pad, which leading surface 26 is closest to the power head 16. Irrigation fluid may be supplied by manual or powered means through the tube 30. With this arrangement, the irrigation fluid is supplied directly to the region where cutting or drilling occurs, and the direction of the flow of the irrigation fluid may be controlled by controlling the orientation of the tool.

A further modification is illustrated in FIGS. 4a to 4d. The pad 20 illustrated in FIGS. 4a to 4d is generally similar to the pad of FIGS. 2a to 2f, and the same reference numerals are used. However, in this arrangement an onlay 40 is positioned on the inner surface 24 of the pad 20. The onlay is of acrylnitrite butadiene styrene [ABS] and provides additional vibration absorption.

Note that the arrangements of FIGS. 4a to 4d may be combined with the arrangements of FIGS. 3a and 3b, so the pad has both an irrigation duct and an onlay.

Figure 5:
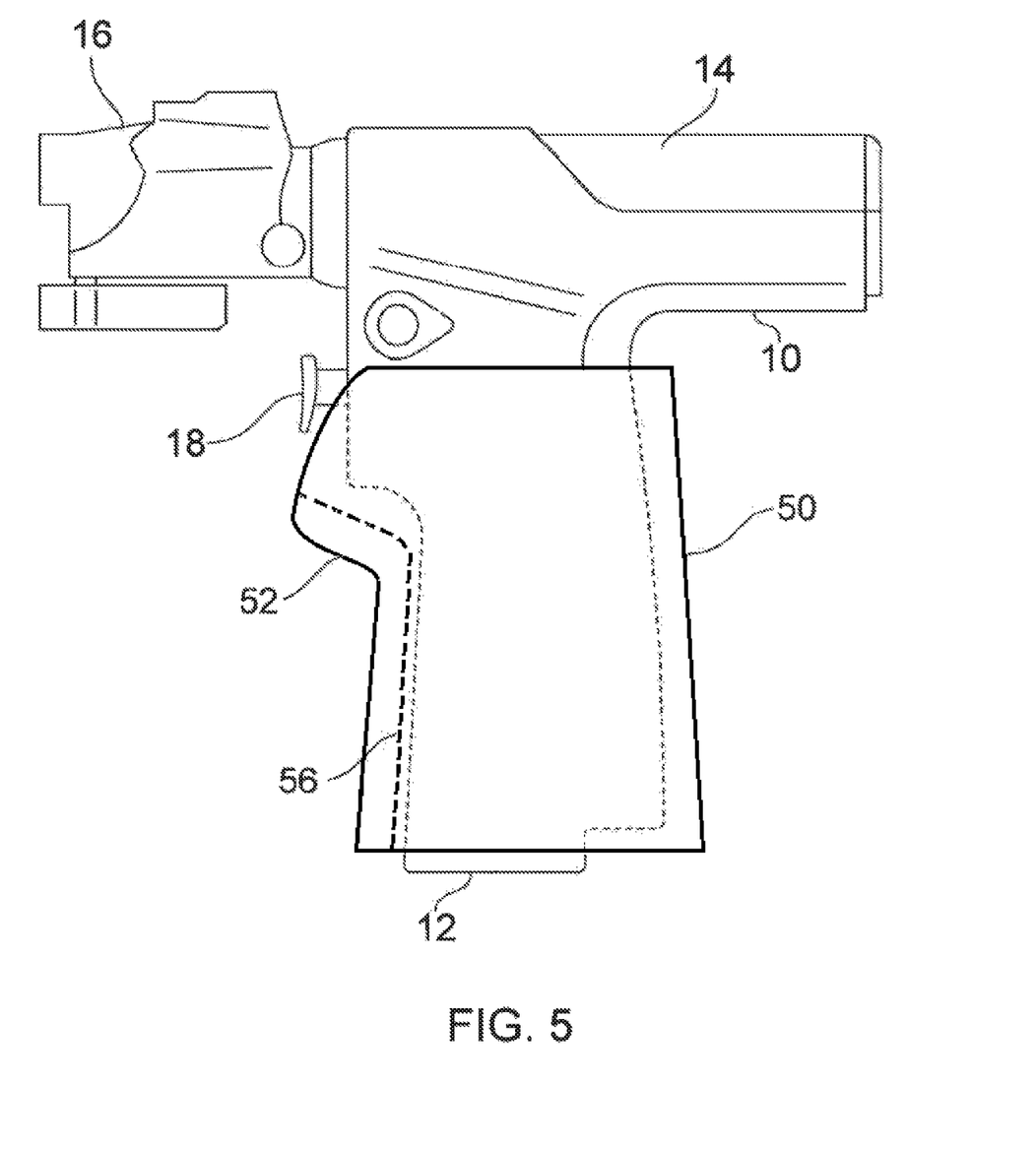
FIG. 5 shows a surgical tool in accordance with another embodiment of present invention.
Figure 6A:
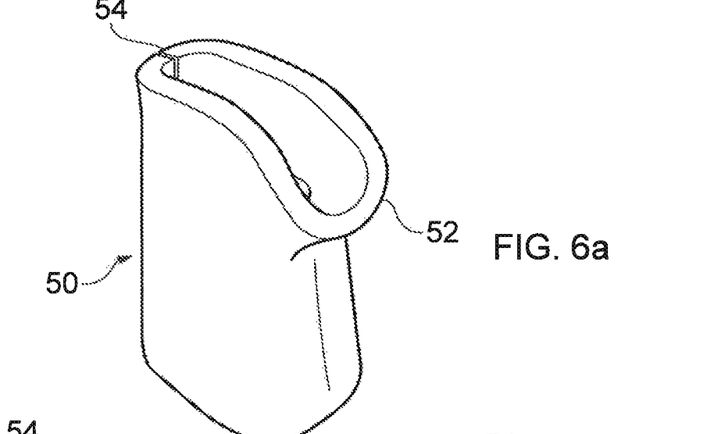
FIGS. 6a through 6d show details of a pad which is part of the surgical tool in accordance with the embodiment of FIG. 5.
Figure 6B:
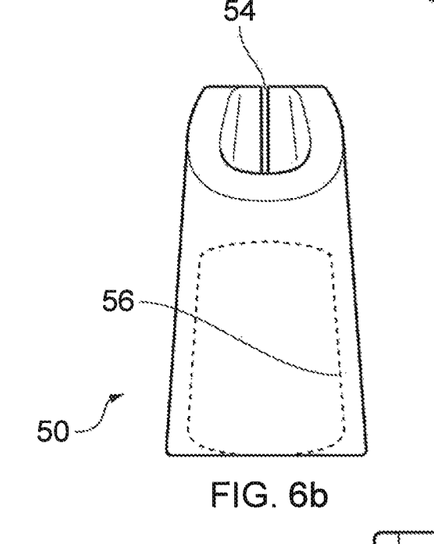
Figure 6C:
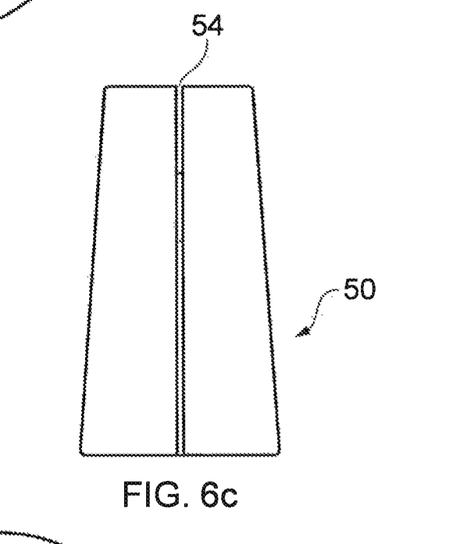
Figure 6D:
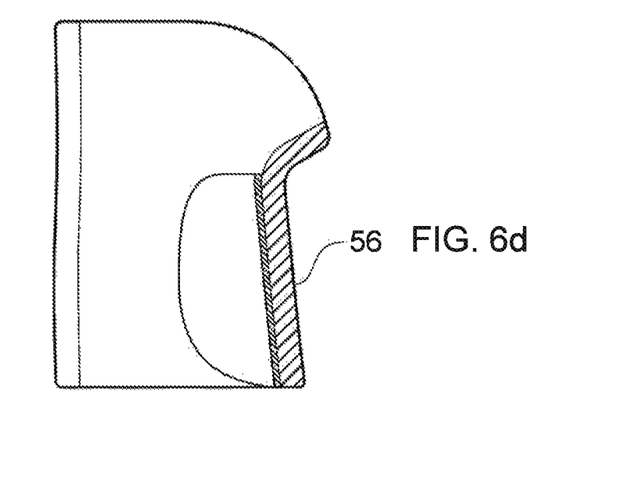

FIG. 5 illustrates how the tool may have a further pad 50 (VM-G pad) mounted on the handle 12. Note that the pad 20 is not shown in FIG. 5, but may be used in an embodiment having two pads. Advantageously, the pad 20 is used with the pad shown in FIG. 5 so that vibration absorbing pads are provided on both the handle 12 and the elongated surface 14, so as to better protect the surgeon.

The pad 50 shown in FIG. 5 is illustrated in more detail in FIGS. 6a to 6d. As this can be seen, it is generally shaped to fit the handle 12, and has a projection part 52 which conforms to the surgeon's hand. A slit 54 in the pad 50 enables it to be fitted around the handle 12. There may be an onlay 56 in a surface of the pad. Again, the onlay 56 is made of ABS.

A modification of the further pad 50 (VM-G pad) is shown in FIGS. 7 and 8a to 8d. It has been found that significant vibration is transmitted via trigger 18 to the user's hand and it is desirable to interpose the material of the pad between that trigger 18 and the user's finger which activates the trigger 18.

Figure 7:
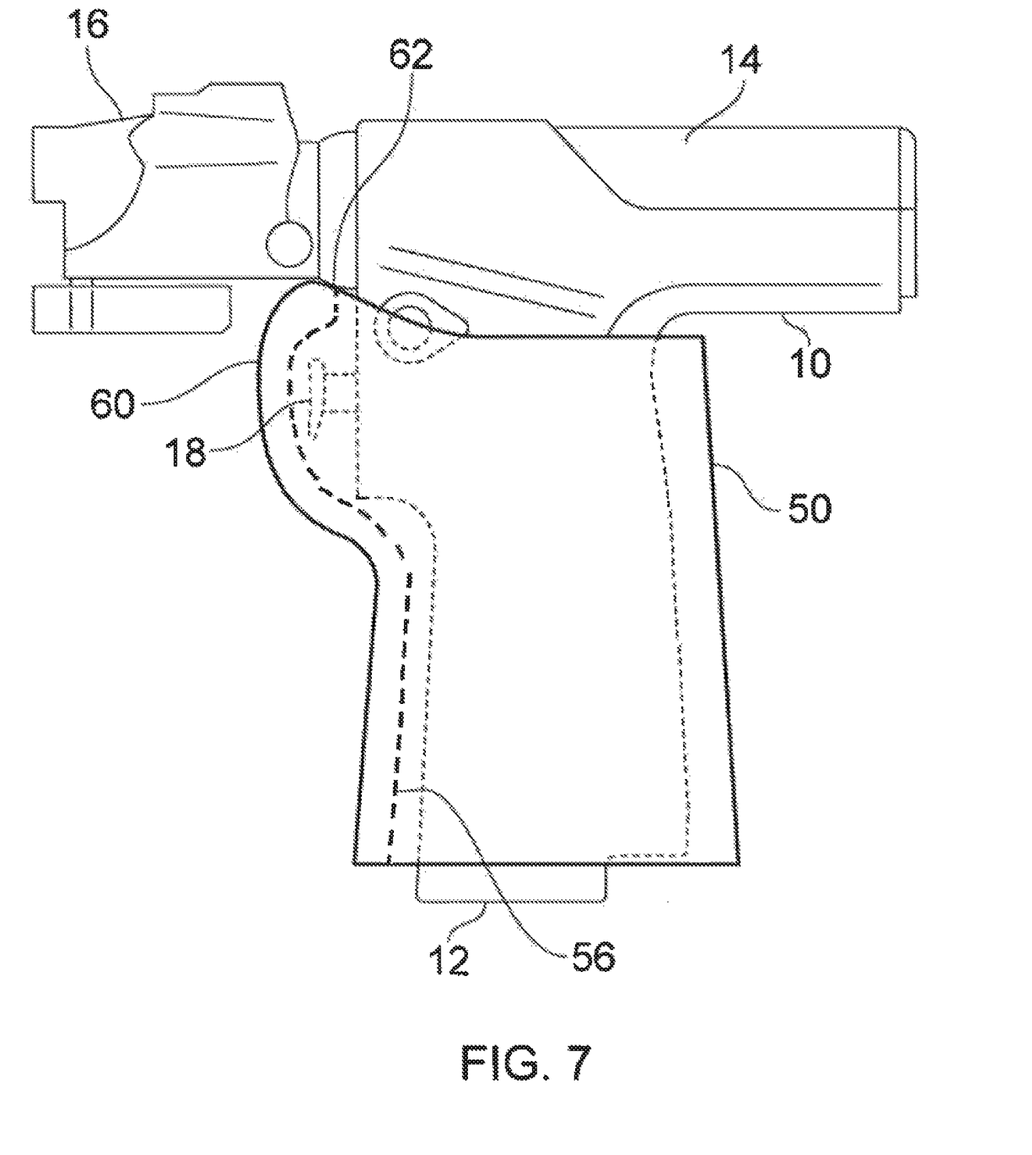
FIG. 7 shows a modification of the pad of FIG. 5.
Figure 8A:
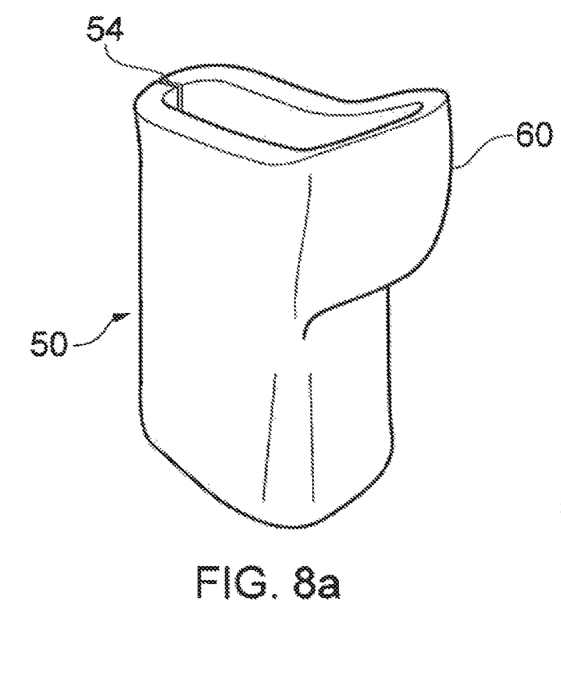
FIGS. 8a through 8d show further modifications to the pad which is a component of certain embodiments of the invention.
Figure 8B:
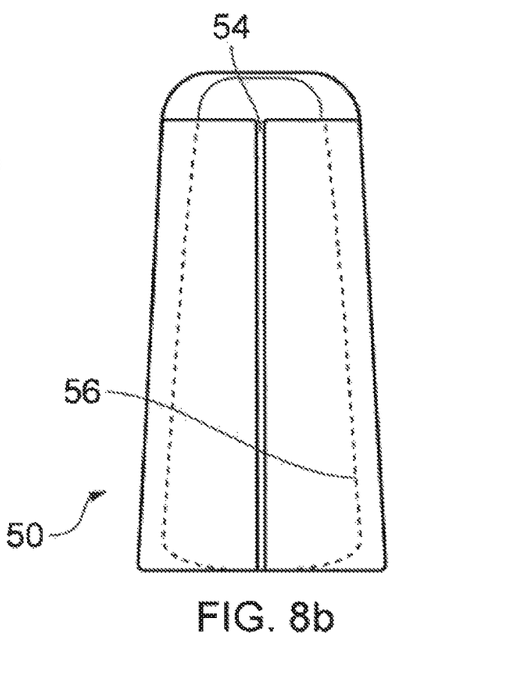
Figure 8C:
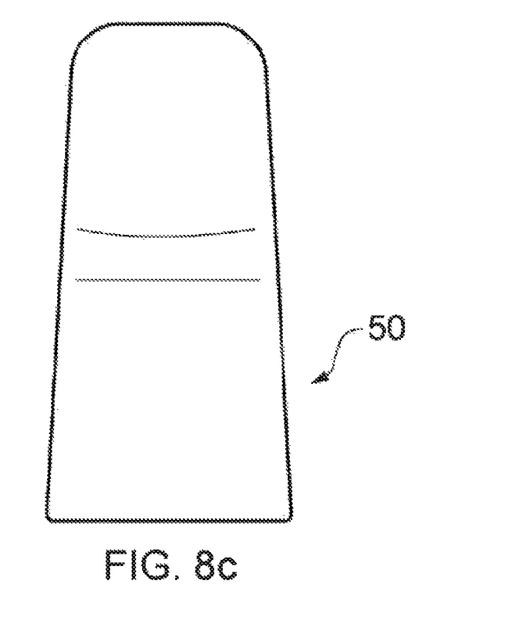
Figure 8D:
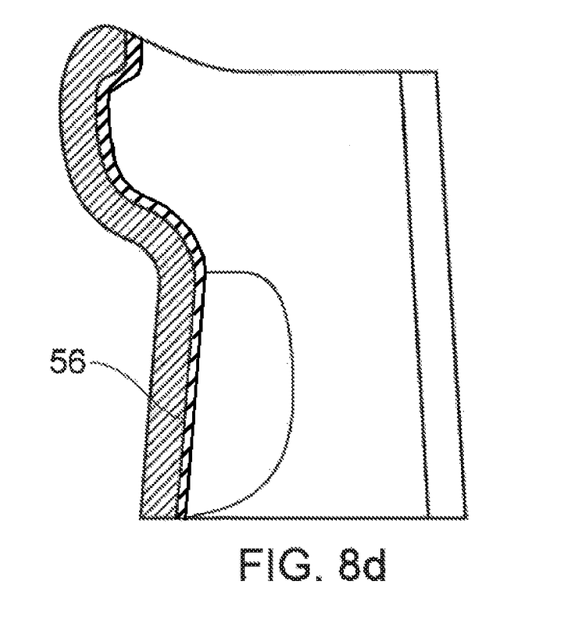

Thus, as shown in FIG. 7, the front of the further pad 50 has an extension 60 which covers the trigger 18 and extends to make contact with the surface 62 of the body 10 of the tool immediately above the trigger 18. Furthermore, as can be seen in FIG. 8a, the extension 60 passes around both sides of the trigger 18, so that no part of the trigger 18 can come into contact with the user's hand, and vibrations are thus absorbed. Again, advantageously the pad 20 is also used with this embodiment, so that two pads are present to better protect the surgeon.

It can also be seen that, in this modification, the slit 54 is at the back of the pad 50 remote from the extension 60, as it not desirable to have any gap in the extension 60 at the front of the pad. The onlay 56 is also at the inner front of the pad.

As shown in FIG. 7, the onlay 56 is spaced from the surface of the tool, so that there is a gap between the onlay 56 and the surface of the tool. The advantage of this arrangement is that it is possible to retain manual dexterity—"feel"—whilst protecting the surgeon's hands. In particular, the surgeon is able to squeeze the pad 50 when holding the tool, and for the pad 50 to be compressed to bring the onlay into contact with the surface of the tool, thereby providing some "give" from the pad 50. In particular, as shown in FIG. 7, the onlay 56 is spaced from the trigger 18, so that when the surgeon releases the trigger 18 by no longer squeezing the pad 50, the trigger 18 is able to return to its original uncompressed position without significant resistance, because there is a gap between the onlay 56 and the trigger 18 for the trigger 18 to extend into.

Although not shown, the onlay 56 is advantageously in contact with the handle of the tool at the lower end of the onlay 56, to provide a pivot point about which the onlay 56 can be pivoted when the trigger is squeezed.

Other aspects and features of the present invention are set out in the following numbered clauses.

1. A hand-held surgical tool having at least one pad of vibration-absorbent material thereon, the pad being of hydrophobic polyurethane foam made from a polyol and isocyanate composition in which the weight ratio of polyol to isocyanate is from 2.5:1 to 1.5:1.

2. A tool according to clause 1, which tool is a saw having a handle being a first hand grip and an elongated surface being a second hand grip.

3. A tool according to clause 2, which is also adopted for bone drilling.

4. A tool according to clause 2 or clause 3, wherein the at least one pad of vibration absorbent material comprises a first pad mounted on the second hand grip.

5. A tool according to clause 4, having a first onlay between the first pad and the second hand grip, the onlay being of acrylonitrile butadiene styrene [ABS].

6. A tool according to clause 4 or clause 5, wherein the weight ratio of the polyol to isocyanate of the first pad is from 8.5:3.9 to 9:5.

7. A tool according to any one of clauses 4 to 6, further including an irrigation duct through the first pad.

8. A tool according to clause 2 or clause 3 wherein the at least one pad of vibration absorbent material comprises a second pad mounted on the first hand grip.

9. A tool according to clause 8, wherein the handle has a trigger extending therefrom for controlling the operation of the tool, and the second pad covers the trigger.

10. A tool according to clause 8 or clause 9, having a second onlay between the second pad and the rest of the tool, the onlay is of acrylonitrile butadiene styrene [ABS].

11. A tool according to any one of clauses 8 to 10, wherein the weight ratio of the polyol to isocyanate of the second pad is from 15:6.8 to 12:6.7.

12. A tool according to any one of the previous clauses, wherein, in the polyol and isocyanate composition that forms the at least one pad:

(i) the polyol comprises 94.8% by weight polyoxyalkylene triols, 1.8% by weight triethanolamine, 0.2% by weight dipropylene glycol, 0.1% by weight triethyldiamine, 0.4% by weight organo-modified polysiloxanes, 2.1% by weight C9-11 alcohol ethoxylate and 0.6% by weight 2-[[2-dimethylamino)ethyl]methylamino] ethanol, and/or (ii) the isocyanate comprises 50% to 77% by weight diphenylmethanediisocyanate, isomers and homologues thereof, and 23% to 50% by weight isocyanates that are the reaction product of the polyol with methylenediphenyldiisocyanate.

13. A hand-held surgical tool having at least one pad of vibration-absorbent material thereon, the pad having an irrigation duct therethrough connected to means for supplying irrigation fluid to the duct.

14. A tool according to clause 7 or clause 13 wherein the irrigation duct terminates at an outer surface of said pad or said first pad.

15. A pad for a hand-held surgical tool, the pad being of hydrophobic polyurethane foam made from a polyol and isocyanate composition in which the weight ratio of polyol to isocyanate is from 2.5:1 to 1.5:1.

16. A pad according to clause 12 wherein the weight ratio of the polyol to isocyanate is from 8.5:3.9 to 9:5 and 15:6.8 to 12:6.7.

17. A pad for a hand-held surgical tool, wherein the pad has an irrigation duct therethrough connected to means for supplying irrigation fluid to the duct.

Although illustrated embodiments of the present invention have been described, it should be understood that various changes, substitutions, and alterations can be made by one of ordinary skill in the art without departing from the present invention which is defined by the recitations in the claims below and equivalents thereof.

The invention claimed is:

1. A hand-held surgical tool comprising at least one pad of vibration-absorbent material thereon, the pad being of hydrophobic polyurethane foam made from a polyol and isocyanate composition in which the weight ratio of polyol to isocyanate is from 2.5:1 to 1.5:1,
   wherein the tool comprises a saw having a handle providing a first hand grip and an elongated surface providing a second hand grip;
   wherein the at least one pad of vibration absorbent material comprises a first pad mounted on the second hand grip, and
   wherein the at least one pad of vibration absorbent material comprises a second pad mounted on the first hand grip.

2. A tool according to claim 1, wherein the tool is adapted for bone drilling.

3. A tool according to claim 1, further comprising a first onlay between the first pad and the second hand grip, the onlay being of acrylonitrile butadiene styrene [ABS].

4. A tool according to claim 1, wherein the weight ratio of the polyol to isocyanate of the first pad is from 8.5:3.9 to 9:5.

5. A tool according to claim 1, further comprising an irrigation duct through the first pad.

6. A tool according to claim 1, wherein the handle has a trigger extending therefrom for controlling the operation of the tool, and the second pad covers the trigger.

7. A tool according to claim 1, further comprising a second onlay between the second pad and the rest of the tool, the onlay being acrylonitrile butadiene styrene [ABS].

8. A tool according to claim 1, wherein the weight ratio of the polyol to isocyanate of the second pad is from 15:6.8 to 12:6.7.

9. A tool according to claim 1, wherein, in the polyol and isocyanate composition that forms the at least one pad:
  (i) the polyol comprises 94.8% by weight polyoxyalkylene triols, 1.8% by weight triethanolamine, 0.2% by weight dipropylene glycol, 0.1% by weight triethyldiamine, 0.4% by weight organo-modified polysiloxanes, 2.1% by weight C9-11 alcohol ethoxylate and 0.6% by weight 2-[[2-dimethylamino)ethyl]methylamino] ethanol, or
  (ii) the isocyanate comprises 50% to 77% by weight diphenylmethanediisocyanate, isomers and homologues thereof, and 23% to 50% by weight isocyanates that are the reaction product of the polyol with methylenediphenyldiisocyanate, or
  (iii) both (i) and (ii).

10. A tool according to claim 5, wherein the irrigation duct terminates at an outer surface of said pad or said first pad.

* * * * *